United States Patent
Evju et al.

(10) Patent No.: US 12,013,363 B2
(45) Date of Patent: Jun. 18, 2024

(54) COMBUSTIBLE GAS SENSOR

(71) Applicant: Carrier Corporation, Palm Beach Gardens, FL (US)

(72) Inventors: Jon K. Evju, Shakopee, MN (US); Gary Follett, Saint Paul, MN (US); Thi A. Nguyen, Champlin, MN (US); David P. Potasek, Lakeville, MN (US); Roger Alan Backman, Minneapolis, MN (US); Anand Venkatesh Sankarraj, Eden Prairie, MN (US); Siqi Wei, Minneapolis, MN (US)

(73) Assignee: CARRIER CORPORATION, Palm Beach Gardens, FL (US)

(*) Notice: Subject to any disclaimer, the term of this patent is extended or adjusted under 35 U.S.C. 154(b) by 787 days.

(21) Appl. No.: 17/059,087

(22) PCT Filed: Nov. 20, 2019

(86) PCT No.: PCT/US2019/062368
§ 371 (c)(1),
(2) Date: Nov. 25, 2020

(87) PCT Pub. No.: WO2020/117472
PCT Pub. Date: Jun. 11, 2020

(65) Prior Publication Data
US 2021/0255131 A1  Aug. 19, 2021

Related U.S. Application Data

(60) Provisional application No. 62/774,581, filed on Dec. 3, 2018.

(51) Int. Cl.
G01N 27/16 (2006.01)
G01N 25/30 (2006.01)
G01N 33/00 (2006.01)

(52) U.S. Cl.
CPC ............. *G01N 27/16* (2013.01); *G01N 25/30* (2013.01); *G01N 33/0027* (2013.01); *G01N 33/005* (2013.01)

(58) Field of Classification Search
CPC ........ G01N 27/14; G01N 27/16; G01N 25/30; G01N 33/0027; G01N 33/005
See application file for complete search history.

(56) References Cited

U.S. PATENT DOCUMENTS 3,959,764 A  5/1976  Allman
4,068,021 A  1/1978  Allman
(Continued)

FOREIGN PATENT DOCUMENTS

CN  103184886 A  7/2013
CN  201110452721 A  7/2013
(Continued)

OTHER PUBLICATIONS

International Search Report and Written Opinion for International Application No. PCT/US2019/062368; International Filing Date Nov. 20, 2019; dated Jun. 25, 2020 (pp. 1-15).

*Primary Examiner* — Benjamin R Schmitt
(74) *Attorney, Agent, or Firm* — CANTOR COLBURN LLP

(57) ABSTRACT

A combustible gas sensor that includes a reference sensor. The reference sensor includes a first substrate having a first substrate first surface, a first insulating layer disposed on the first substrate first surface, and a first heater at least one of embedded within the first insulating layer and disposed on the first insulating layer. The first substrate is a MEMS substrate.

17 Claims, 2 Drawing Sheets

(56) References Cited

U.S. PATENT DOCUMENTS

| | | | |
|---|---|---|---|
| 4,123,225 A * | 10/1978 | Jones | G01N 27/16 |
| | | | 338/34 |
| 4,560,585 A | 12/1985 | Khilnani | |
| 4,720,421 A | 1/1988 | Khilnani | |
| 5,451,371 A | 9/1995 | Zanini-Fisher et al. | |
| 5,451,920 A * | 9/1995 | Hoffheins | G01N 33/005 |
| | | | 338/307 |
| 5,464,966 A | 11/1995 | Gaitan et al. | |
| 5,834,627 A | 11/1998 | Ricco et al. | |
| 5,902,556 A | 5/1999 | Van De Vyver et al. | |
| 6,095,681 A | 8/2000 | Kunt et al. | |
| 6,111,280 A | 8/2000 | Gardner et al. | |
| 6,165,336 A * | 12/2000 | Maki | G01N 33/497 |
| | | | 427/244 |
| 6,419,880 B1 | 7/2002 | Pasquariello | |
| 6,539,774 B1 | 4/2003 | Zinck et al. | |
| 6,663,834 B1 | 12/2003 | Miller et al. | |
| 6,786,716 B1 | 9/2004 | Gardner et al. | |
| 7,911,010 B2 | 3/2011 | Stetter | |
| 8,024,952 B2 | 9/2011 | Hossler et al. | |
| 8,211,586 B2 | 7/2012 | Nakakubo | |
| 8,426,932 B2 | 4/2013 | Stetter | |
| 8,501,101 B2 * | 8/2013 | Chen | G01N 27/127 |
| | | | 422/94 |
| 8,573,030 B2 | 11/2013 | Gole | |
| 8,884,382 B2 | 11/2014 | Stetter et al. | |
| 8,931,950 B2 | 1/2015 | King et al. | |
| 9,182,366 B2 | 11/2015 | Izawa et al. | |
| 9,829,455 B2 | 11/2017 | Watanabe et al. | |
| 9,945,803 B2 | 4/2018 | Suzuki | |
| 2002/0146352 A1 * | 10/2002 | Wang | G01N 27/16 |
| | | | 422/94 |
| 2003/0057109 A1 * | 3/2003 | Wang | G01N 27/4072 |
| | | | 204/426 |
| 2007/0212263 A1 | 9/2007 | Shin et al. | |
| 2009/0312954 A1 | 12/2009 | Utriainen | |
| 2012/0138459 A1 * | 6/2012 | Chen | G01N 27/127 |
| | | | 204/424 |
| 2014/0208838 A1 | 7/2014 | Moon et al. | |
| 2016/0077032 A1 | 3/2016 | Hattori | |
| 2018/0106745 A1 | 4/2018 | Shibasaki et al. | |
| 2018/0128763 A1 | 5/2018 | Swanson et al. | |

FOREIGN PATENT DOCUMENTS

| | | |
|---|---|---|
| CN | 105758899 A | 7/2016 |
| JP | 2012172973 A | 9/2012 |
| WO | 2005078422 A1 | 8/2005 |

* cited by examiner

COMBUSTIBLE GAS SENSOR

CROSS REFERENCE TO RELATED APPLICATIONS

This application is a US National Stage of International Application No. PCT/2019/062368 filed Nov. 20, 2019, which claims the benefit of U.S. Application No. 62/774,581, filed on Dec. 3, 2018, which are incorporated herein by reference in their entirety.

BACKGROUND

Exemplary embodiments pertain to the art of combustible gas sensors.

Catalytic bead combustible gas sensors are employed to detect the presence of combustible gases or combustible vapors such that a warning of a potentially hazardous condition may be provided. Commonly these combustible gas sensors are handmade which may result in variations in product quality and may be time-consuming to manufacture.

BRIEF DESCRIPTION

Disclosed is a combustible gas sensor that includes a reference sensor. The reference sensor includes a first substrate having a first substrate first surface, a first insulating layer disposed on the first substrate first surface, and a first heater at least one of embedded within the first insulating layer and disposed on the first insulating layer.

In addition to one or more of the features described above, or as an alternative to any of the foregoing embodiments, the first substrate is MEMS substrate.

In addition to one or more of the features described above, or as an alternative to any of the foregoing embodiments, the MEMS substrate is made of at least one of silicon, Si3N4 (silicon nitride), SiC (silicon carbide), beryllium oxide, quartz, ceramics, aluminum nitride, silica, or sapphire.

In addition to one or more of the features described above, or as an alternative to any of the foregoing embodiments, the reference sensor includes a glaze disposed on the first insulating layer, the glaze being arranged as a passivating non-porous glassy layer.

In addition to one or more of the features described above, or as an alternative to any of the foregoing embodiments, the reference sensor includes an electrical connector that extends through the first insulating layer and is connected to the first heater.

In addition to one or more of the features described above, or as an alternative to any of the foregoing embodiments, an active sensor is disposed adjacent to the reference sensor. The active sensor includes a second substrate having a second substrate first surface, a second insulating layer disposed on the second substrate first surface, a second heater at least one of embedded within the second insulating layer and disposed on the second insulating layer, and a catalyst layer disposed on the second insulating layer.

In addition to one or more of the features described above, or as an alternative to any of the foregoing embodiments, the second substrate is a MEMS substrate.

In addition to one or more of the features described above, or as an alternative to any of the foregoing embodiments, the MEMS substrate is made of at least one of silicon, aluminum nitride, alumina, and sapphire.

In addition to one or more of the features described above, or as an alternative to any of the foregoing embodiments, the active sensor includes an anti-poison layer disposed on the catalyst layer, the anti-poison layer defining a plurality of openings.

In addition to one or more of the features described above, or as an alternative to any of the foregoing embodiments, the active sensor includes an electrical connector that extends through the second insulating layer and is connected to the second heater.

Also disclosed is a combustible gas sensor that includes a reference sensor and an active sensor. The reference sensor includes a first substrate having a first substrate first surface and a first substrate second surface disposed opposite the first substrate first surface, a first insulating layer disposed on the first substrate first surface, and a first heater embedded within the first insulating layer. The active sensor is disposed adjacent to the reference sensor and includes a second substrate having a second substrate first surface and a second substrate second surface disposed opposite the second substrate first surface, a second insulating layer disposed on the second substrate first surface, a second heater embedded within the second insulating layer, a catalyst layer disposed on the second insulating layer, and a first anti-poison layer disposed on the catalyst layer, the first anti-poison layer defining a first plurality of openings.

In addition to one or more of the features described above, or as an alternative to any of the foregoing embodiments, the first substrate is made of a thermally conductive material.

In addition to one or more of the features described above, or as an alternative to any of the foregoing embodiments, the reference sensor includes a third insulating layer disposed on the first substrate second surface.

In addition to one or more of the features described above, or as an alternative to any of the foregoing embodiments, the reference sensor includes a glaze disposed on the third insulating layer.

In addition to one or more of the features described above, or as an alternative to any of the foregoing embodiments, the second substrate is made of a thermally conductive material.

In addition to one or more of the features described above, or as an alternative to any of the foregoing embodiments, the active sensor includes a fourth insulating layer disposed on the second substrate second surface.

In addition to one or more of the features described above, or as an alternative to any of the foregoing embodiments, the active sensor includes a second anti-poison layer disposed on the fourth insulating layer, the second anti-poison layer defining a second plurality of openings.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1A:
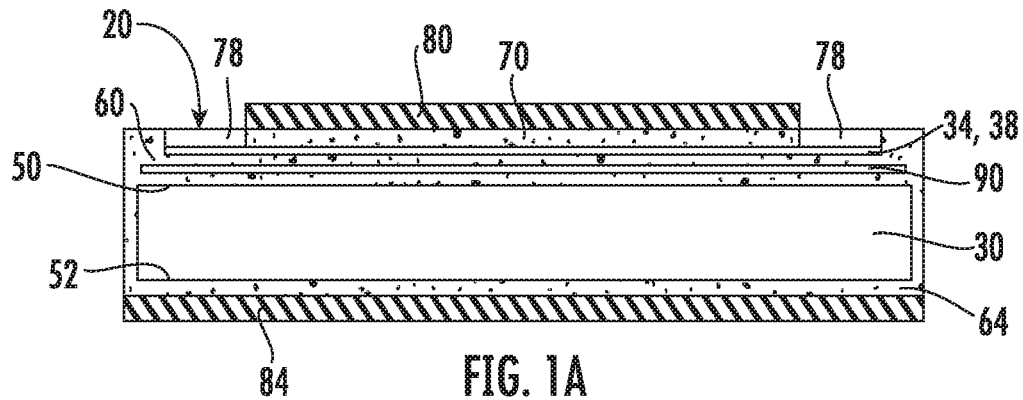
FIG. 1A is a cross section view of a first exemplary reference sensor of a MEMS based combustible gas sensor.
Figure 1B:
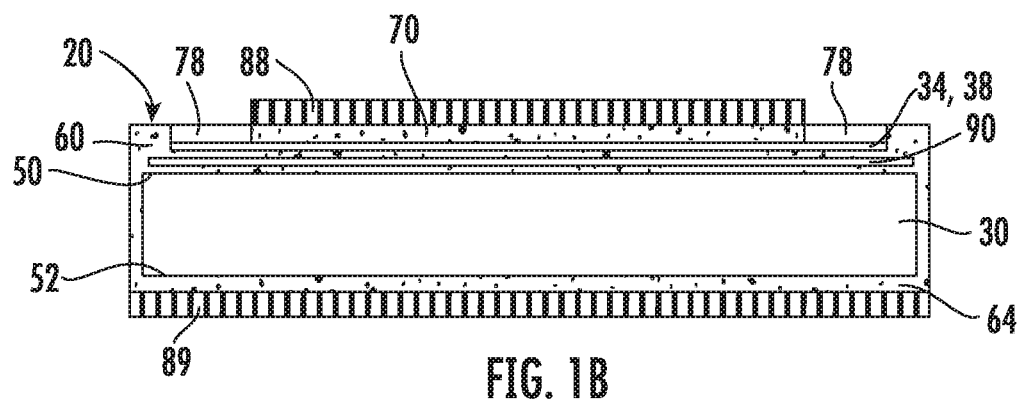
FIG. 1B is a cross section view of a first exemplary reference sensor of a MEMS based combustible gas sensor.
Figure 2:
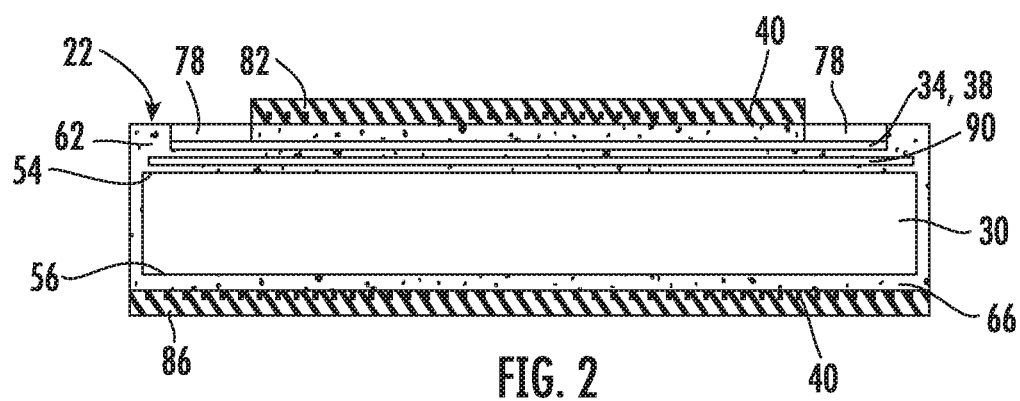
FIG. 2 is a cross-section view of an active sensor of the MEMS based combustible gas sensor.
Figure 3:
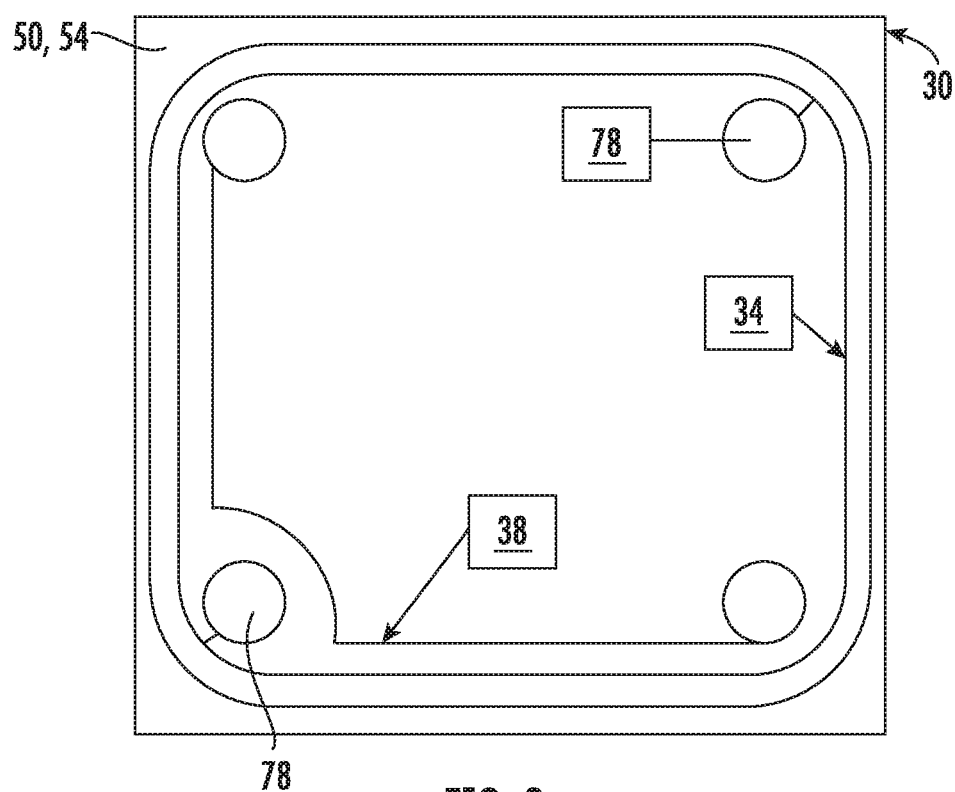
FIG. 3 is a plan view of a MEMS substrate.

Referring to FIGS. 1-3, a first sensor or a reference sensor 20, a second sensor or an active sensor 22, and a MEMS based substrate 30 of a combustible gas sensor is shown. The combustible gas sensor is used for detection of combustible gases in certain environments, such as hazardous environments.

The active sensor 22 abuts or may be disposed adjacent to the reference sensor 20. The reference sensor 20 and the active sensor 22 are both heated or idled to within a predetermined temperature range. The additional heat from catalytically aided oxidation of combustible gases or combustible vapors may raise or increase a temperature of the active sensor 22, resulting in a measurable temperature difference across the active sensor 22 relative to the reference sensor 20, enabling the determination of combustible gases or combustible vapor concentrations. Combustible gas or combustible vapor concentrations may be derived from the resistance increase or temperature difference between the active sensor 22 and the reference sensor 20.

The reference sensor 20 and the active sensor 22 each include a substrate 30, a heater 34, and a temperature sensor 38. Both the reference and active sensors 20, 22 may contain an embedded lateral heat transfer device 90, as will be discussed later, to facilitate lateral heat transfer between the heater 34, the temperature sensor 38, and a catalyst layer 40 of the active sensor 22. Unlike the reference sensor 20, the active sensor 22 is provided with the catalyst layer 40 that enables the active sensor 22 to react to the presence of combustible gases or combustible vapors. The application of the catalyst layer 40 and the anti-poison layers may be repeated multiple times. The application of catalyst layer and anti-poison layer in multiple alternating layers allows the build-up of reserve catalyst into the system in case the catalyst becomes mobile during manufacturing of the combustible gas sensor or while the combustible gas sensor is in use.

The substrate 30 comprises a thermally conductive material that is capable of operating at high temperatures within a range of approximately 600-800° C. for the duration of a sensor's lifetime. In at least one embodiment, substrates comprising less thermally conductive materials may be used, in these applications, the lateral heat transfer device 90 aids the uniformity and flow of heat within the reference and active sensors 20, 22. The lateral heat transfer device 90 is a very good conductor of heat that spreads the heat generated during a sensing event towards the temperature sensor 38 to increase the speed of detection of the combustible gas sensor 10.

The substrate 30 may be provided with adhesion layers, diffusion barriers, and dielectrics that inhibit the substrate 30 from decomposing or degrading such that the combustible gas sensor is stable at these high temperatures. The substrate adhesion layers, diffusion barriers and dielectrics have been chosen so that the substrate 30 does not decompose and the combustible gas sensor is stable at these high temperatures. The MEMS-based substrate 30 provides distinct advantages over the traditional handmade, hand-painted ceramic substrate having a lower thermal conductivity. The MEMS-based substrate 30 may be made of silicon, $Si_3N_4$ (silicon nitride), SiC (silicon carbide), beryllium oxide, quartz, ceramics (e.g. steatite, porcelain, alumina), aluminum nitride, silica, sapphire, or other suitable material that is itself thermally conductive, or includes an embedded lateral heat transfer device 90, in order to enable the heater 34 to more uniformly, consistently, and quickly heat the substrate 30.

The MEMS-based substrate 30 reduces drift, improves reliability, improves repeatability of production through the implementation of an automated process or batch processing to produce substantially similar parts, decreases production costs and increases the lifetime of the combustible gas sensor. The MEMS-based substrate is robust enough to allow for the application of films or layers onto the substrate 30 (e.g. from thin film deposition techniques such as physical or chemical vapor deposition processes) or thick film deposition techniques (e.g. spraying, electro spinning, screen printing or inkjet printing), in addition to the traditional hand painting or dipping that is done on traditional ceramic combustible gas sensor substrates. Combinations of all or some of these application techniques may be used in building these sensors. In addition to being used as actual sensor coatings, all these methods may also be used to deposit sacrificial 3D templates for catalyst and oxide depositions, increasing the sensor surface area and creating effective torturous path catalyst anti-poisoning layers.

The substrate 30 may be in wafer form. The substrate 30 may be smooth, etched, or rough and may be prepared using clean room compatible techniques. The reference sensor 20 and the active sensor 22 may be manufactured in pairs from the same wafer. This may ensure that the remaining elements of each sensor undergo substantially the same treatment and have substantially the same thermal masses to ensure that the reference sensor 20 and the active sensor 22 are as similar as possible in the absence of combustible gases. The reference sensor 20 and the active sensor 22 may be bridged or spaced apart from each other.

Referring to FIGS. 1A, 1B, and 2, the substrate 30 associated with the reference sensor 20 may be a first substrate having a first substrate first surface 50 and a first substrate second surface 52 that is disposed opposite the first substrate first surface 50. The substrate 30 associated with the active sensor 22 may be a second substrate having a second substrate first surface 54 and a second substrate second surface 56 that is disposed opposite the second substrate first surface 54.

Insulating layers may be disposed on or about the first substrate associated with the reference sensor 20 and the second substrate associated with the active sensor 22. In at least one embodiment, the insulating layers completely encapsulate the substrate 30 and the lateral heating device 90. The insulating layers may be dielectric layers made of or including $Si_3N_4$, $SiO_2$, $Al_2O_3$, or the like.

A first insulating layer 60 may be disposed on the first substrate first surface 50. A second insulating layer 62 may be disposed on the second substrate first surface 54. In some embodiments, additional insulating layers may be applied to the second surfaces of the respective substrates. In such embodiments, a third insulating layer 64 may be disposed on the first substrate second surface 52 and a fourth insulating layer 66 may be disposed on the second substrate second surface 56.

The catalyst layer 40 is disposed on the second insulating layer 62 of the active sensor 22. In at least one embodiment, the catalyst layer 40 may be disposed on the second substrate first surface 54. The catalyst layer 40 may also be disposed on the fourth insulating layer 66 of the active sensor 22, giving the active sensor 22 two-sided detection capabilities.

The catalyst layer 40 may include a transition metal based catalyst, such as platinum, palladium, or other transition metal catalysts that lower the activation energy for oxidation of combustible gases. The catalyst layer 40 may be applied using a thin film application technique such as sputtering, physical or chemical vapor deposition, evaporation, inkjet printing, painting, spraying, electrospinning, spraying, screen printing, or in combination with these or catalyst or catalyst precursors.

In at least one embodiment, the catalyst layer 40 may be combined with the anti-poison layers, or anti-poison template layers, as nanoparticles or as a molecular precursor and applied together onto insulating layers 62, 66 along with the anti-poison layers 82, 86 on the active sensor 22.

The reference sensor 20 does not have an exposed active catalyst layer 40. The reference sensor 20 does otherwise have substantially similar coatings as does the active sensor 22. In one embodiment, the reference sensor 20 has all of the coating layers of the active sensor 22, except the catalyst layers 40. In another embodiment, the reference sensor 20 may be provided with a catalyst layer 40 that is entirely encapsulated by a glassy coating to prevent exposure of the catalyst layer 40 on the reference sensor 40 to an external environment as well as to make the reference sensor 20 more robust by protecting the heater 34 and the temperature sensor 38 from exposure to the external environment.

Heat generated by the oxidation of the catalyst layer 40 of the active sensor 22 in the presence of combustible gases on the catalyst layer 40 may be transferred to or detected by the temperature sensor 38 associated with the active sensor 22. The temperature of the active sensor 22 may be compared to a temperature detected by the temperature sensor 38 associated with the reference sensor 20 to enable a controller or a processor in communication with the combustible gas sensor to determine whether combustible gases are present or are detected.

The heater 34 may be disposed or embedded within the insulating layers 60, 62, 64, 66, as shown in FIGS. 1A, 1B, and 2, disposed on or integrated with the substrate 30, or may be disposed on the insulating layers 60, 62, 64, 66. The heater 34 may be disposed on the first substrate first surface 50 and/or on the second substrate first surface 54, as shown in FIG. 3. The heater 34 extends about the substrate 30 and is spaced apart from the temperature sensor 38. The heater 34 and the temperature sensor 38 are provided on different circuits to prevent crosstalk between the circuits.

The heater 34 and the temperature sensor 38 are deposited on the same insulating layer or same substrate surface but are spaced apart from each other and are not electrically connected to each other.

The heater 34 may be a resistive heater such as a gold, iridium, nickel, copper, nichrome, platinum, or alloys of the aforementioned. The insulating layers 60, 62, 64, 66 prevent the heater 34 from being exposed to the sensing environment, thus eliminating slow sensor drift due to changing resistance and the conductor associated with the heater 34 over time.

The heater 34 associated with the reference sensor 20, e.g. a first heater, may be embedded within or disposed on the first insulating layer 60 or may be disposed on or embedded within the first substrate first surface 50. The heater 34 associated with the active sensor 22, e.g. a second heater, may be embedded within or disposed on the second insulating layer 62 or may be disposed on or embedded within the second substrate first surface 54. The heater 34 is arranged to uniformly heat the substrate 30 to a predetermined temperature to facilitate operation of the combustible gas sensor. The temperature sensor 38 allows for precise temperature control of the substrate 30. The temperature sensor 38 may be a resistive temperature detector. The combination of the heater 34 and the temperature sensor 38 lends itself to electronic feedback circuitry and controls that ensure stable or consistent temperature operation across the substrate 30 with changing ambient conditions and eliminates high temperature excursions of the substrate 30 or the combustible gas sensor that may impact the sensor surfaces and change the sensor's response to the presence of combustible gases or combustible vapors. The temperature sensor 38 improves the ease of measurement of the temperature of each element of the combustible gas sensor 10 and operates the elements at constant temperatures in an isothermal operating mode. The combustible gas sensor 10 also uses the differential heat input between the reference sensor 20 and active sensor 22 to estimate concentrations of combustible gases. In a constant current operation mode of the combustible gas sensor 10, the reaction of the catalyst layer 40 of the active sensor 22 with the combustible gas increases the electrical resistance of the active sensor 22 leading to a voltage increase and a temperature increase of the active sensor 22 that may potentially lead to a "high temperature excursion." The active control of the temperature of the active sensor 22 through the feedback provided by the temperature sensor 38 adjusts the heater 34 temperature to inhibit potential temperature excursions. In a constant voltage operation mode of the combustible gas sensor 10, the reaction of the catalyst layer 40 of the active sensor 22 with the combustible gas increases the electrical resistance of the active sensor 22, however the limiting of the voltage limits temperature increases of the active sensor 22.

An electrical connector 78 extends through the first insulating layer 60 and connects the heater 34 to a power source. The electrical connector 78 may be a bond pad. The heater 34 is disposed about the electrical connector 78.

The temperature sensor 38 enables the MEMS-based combustible gas sensor to be controlled at a constant temperature. Upon the substrate 30 achieving a steady state or constant temperature, a controller that is in communication with the heater 34 and the temperature sensor 38 of the combustible gas sensor may monitor the difference between the applied heater voltage or heater power between the heater 34 of the reference sensor 20 and heater 34 of the active sensor 22 to provide means for estimating the combustible gas concentrations.

In at least one embodiment, the heater 34 of the reference sensor 20 and the heater 34 of the active sensor 22 may heat their respective substrates 30 to a temperature greater than the operating temperature of the combustible gas sensor to clean off coking or other contaminants from the sensing surfaces of the combustible gas sensor.

In at least one embodiment, the operating or idling temperature of the combustible gas sensor may be cycled, modulated, or varied by the heater 34 associated with either the reference sensor 20 and/or the active sensor 22 to enable the combustible gas sensor to positively identify a target combustible gas or combustible vapor as the heat of combustion on a sensor surface of the combustible gas sensor changes with temperature.

The anti-poison layers 80, 82, 84, 86 may be provided on both the reference and active sensor 20, 22 surfaces to keep their surface areas and thus heat losses similar. The anti-poison layers 82, 86 on the active sensor 22 reduce coking on the surface and poisoning of the catalyst layer 40. The anti-poison layers 80, 82, 84, 86 may be made of non-catalytic porous materials that effectively trap catalyst poisons and keeps the catalyst poisons from reaching the catalyst layer 40. The anti-poison layers 80, 82, 84, 86 may be coatings that prevent small amounts of volatile silicon bearing compounds from breaking down into silicone oxide and related compounds at the operating temperature of the combustible gas sensor and coating various surfaces of the combustible gas sensor.

The anti-poison layers 80, 82, 84, 86 may be a high surface area porous silica, alumina, or other oxide or mixtures of oxides. The anti-poison layers 80, 82, 84, 86 may have openings that are engineered to reduce airborne silicones or other contaminants' likelihood of reaching and poisoning the catalyst layer 40. The plurality of openings and their associated paths to the catalyst layer 40 are sized to reduce the probability of larger and heavier catalyst poison molecules reaching the catalyst layer 40. The pore size of the anti-poison layers 80, 82, 84, 86 may also be used to selectively trap smaller molecules and exclude larger molecules depending on the size of the target molecules. For example, should the target molecule be hydrogen, the pore size may be small and should the target molecule be methane, the pore size may be larger. The silicones that may poison the catalyst layer 40 are larger than the power size and would not fit through the pores, therefore the pores are sized to exclude large molecules and protect against the poisoning of the catalyst layer 40.

Referring to FIG. 1A, an anti-poison layer 80 may be disposed on the first insulating layer 60 of the reference sensor 20. In at least one embodiment, the anti-poison layer 80 may be disposed on an insulating layer 70 that is disposed adjacent to the heater 34. The anti-poison layer 80 may be laterally disposed between electrical connectors 78 that extend through the first insulating layer 60. The anti-poison layer 80 defines a plurality of openings that define a torturous path.

Referring to FIG. 1B, a glaze 88 may be disposed on the first insulating layer 60 or the insulating layer 70 of the reference sensor 20. The glaze 88 increases the robustness of the reference sensor 20 by encapsulating and protecting the entire reference sensor structure. The glaze 88 may be arranged as a passivating non-porous glassy layer that covers the reference sensor 20 to prevent gases from reaching the heater 34 and the temperature sensor 38.

Referring to FIG. 2, a first anti-poison layer 82 is disposed on the catalyst layer 40 of the active sensor 22. The first anti-poison layer 82 defines a plurality of openings that define a torturous path to the catalyst layer 40 to facilitate the trapping of potential contaminants by the first anti-poison layer 82. The torturous path may be channels, tunnels, openings, that exist in the sponge like material of the first anti-poison layer 82 that keep species that may poison the catalyst layer 40 while allowing combustible gas molecules to reach the catalyst layer 40. The first anti-poison layer 82 and the catalyst layer 40 may be disposed laterally between electrical connectors 78 that extend through the second insulating layer 62.

Referring to FIG. 1A, an anti-poison layer 84 may be disposed on the third insulating layer 64 of the reference sensor 20. The anti-poison layer 84 defines a plurality of openings that define a torturous path.

Referring to FIG. 1B, a glaze 89 may be disposed on the third insulating layer 64 of the reference sensor 20. The glaze 89 may be arranged as a passivating non-porous glassy layer that covers the reference sensor 20.

Referring to FIG. 2, a second anti-poison layer 86 is disposed on the catalyst layer 40 that may be disposed on the fourth insulating layer 66 of the active sensor 22. The second anti-poison layer 86 defines a plurality of openings that define a torturous path.

Referring to FIGS. 1A, 1B, and 2, a heat transfer layer or lateral heat transfer device 90 may be embedded in the insulating layers 60, 62, 64, 66. The heat transfer layer or lateral heat transfer device 90 may be disposed between the heater 34 and the first surface 50, 54 of the substrate 30. The heat transfer layer or device 90 consists of a good conductor of heat (e.g. silicon, aluminum, copper, gold, silver or other suitable material). The heat transfer layer or device 90 aids the transfer of heat between various parts of the sensor and promotes uniform temperatures laterally between the heater and the resistive temperature device.

The use of the MEMS-based substrate 30 for both the reference sensor 20 and the active sensor 22 makes the reference sensor 20 and the active sensor 22 substantially similar to each other. The substantial similarity between the sensors, due to the MEMS-based substrate 30 as well as the layers, enables the reference sensor 20 and the active sensor 22 to be balanced to more consistently measure resistance, voltage, applied current, or temperature of the active sensor 22, based on the operating mode of the combustible gas sensor 10, and compare such measurements to the reference sensor 20. The comparison of these measurements are used to determine detected gas concentrations using a lookup table or other methods.

The combustible gas sensor of the present disclosure employing a MEMS-based substrate 30 reduces labor costs, quality variation, and manufacturing time, by employing automated processes instead of the previously handmade combustible gas sensors. The employing of a MEMS-based substrate 30 also eliminates zero drift mechanisms of the combustible gas sensor. The addition of the anti-poison layers 80, 82, 84, 86 protects the heater 34, the temperature sensor 38, and/or the catalyst layer 40 from exposure to contaminants or poisons due to the torturous paths, ensuring effective performance of the combustible gas sensor.

The reference sensor 20 and the active sensor 22 may be actively temperature controlled by the heater 34 and the temperature sensor 38, so that temperature spikes during combustible gas detection are avoided by adjusting the temperature of the substrate 30 with the heater 34. The active temperature control of the combustible gas sensor 10 decreases the power required to maintain the substrate 30 at a predetermined operating temperature.

With the ease that these sensors are be replicated on large arrays or wafers holding either reference sensors 20 or active sensors 22, spare individual sensor elements can be protected by thermally decomposable coatings that prolong gas detector lifetime and decrease the rate of sensor replacements and calibrations in the field.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A combustible gas sensor, comprising:
a reference sensor, comprising:
a first substrate having a first substrate first surface,
a first insulating layer disposed on the first substrate first surface,
a first heater at least one of embedded within the first insulating layer and disposed on the first insulating layer, and
a first electrical connector that extends through the first insulating layer and is connected to the first heater; and
an active sensor disposed adjacent to the reference sensor, the active sensor comprising:
a second substrate having a second substrate first surface,
a second insulating layer disposed on the second substrate first surface,
a second heater at least one of embedded within the second insulating layer and disposed on the second insulating layer,
a catalyst layer disposed on the second insulating layer,
an anti-poison layer disposed on the catalyst layer, the anti-poison layer defining a plurality of openings, and the anti-poison layer made of a non-catalytic porous material, and
a second electrical connector that extends through the second insulating layer and is connected to the second heater,
wherein the anti-poison layer is laterally disposed between the first electrical connector and the second electrical connector.

2. The combustible gas sensor of claim 1, wherein the first substrate is MEMS substrate.

3. The combustible gas sensor of claim 2, wherein the MEMS substrate is made of at least one of silicon, Si3N4 (silicon nitride), SiC (silicon carbide), beryllium oxide, quartz, ceramics, aluminum nitride, silica, or sapphire.

4. The combustible gas sensor of claim 1, the reference sensor further comprising:
a glaze disposed on the first insulating layer, the glaze being arranged as a passivating non-porous glassy layer.

5. The combustible gas sensor of claim 4, wherein:
the first heater is embedded within the first insulating layer.

6. The combustible gas sensor of claim 1, wherein the second substrate is a MEMS substrate.

7. The combustible gas sensor of claim 6, wherein the MEMS substrate is made of at least one of silicon, aluminum nitride, silicon carbide, beryllium oxide, quartz, and sapphire.

8. The combustible gas sensor of claim 1, wherein:
the second heater is embedded within the second insulating layer.

9. A combustible gas sensor, comprising:
a reference sensor, comprising:
a first substrate having a first substrate first surface and a first substrate second surface disposed opposite the first substrate first surface,
a first insulating layer disposed on the first substrate first surface,
a first heater embedded within the first insulating layer, and
a first electrical connector that extends through the first insulating layer and is connected to the first heater; and
an active sensor disposed adjacent to the reference sensor, the active sensor comprising:
a second substrate having a second substrate first surface and a second substrate second surface disposed opposite the second substrate first surface,
a second insulating layer disposed on the second substrate first surface,
a second heater embedded within the second insulating layer,
a catalyst layer disposed on the second insulating layer,
a first anti-poison layer disposed on the catalyst layer, the first anti-poison layer defining a first plurality of openings, and
a second electrical connector that extends through the second insulating layer and is connected to the second heater,
wherein the first anti-poison layer is laterally disposed between the first electrical connector and the second electrical connector.

10. The combustible gas sensor of claim 9, wherein the first substrate is made of a thermally conductive material.

11. The combustible gas sensor of claim 9, the reference sensor further comprising:
a third insulating layer disposed on the first substrate second surface.

12. The combustible gas sensor of claim 11, the reference sensor further comprising:
a glaze disposed on the third insulating layer.

13. The combustible gas sensor of claim 9, wherein the second substrate is made of a thermally conductive material.

14. The combustible gas sensor of claim 9, the active sensor further comprising:
a fourth insulating layer disposed on the second substrate second surface.

15. The combustible gas sensor of claim 14, the active sensor further comprising:
a second anti-poison layer disposed on the fourth insulating layer, the second anti-poison layer defining a second plurality of openings.

16. The combustible gas sensor of claim 9, wherein the catalyst layer is disposed laterally between the first electrical connector and the second electrical connector.

17. The combustible gas sensor of claim 9, wherein the first anti-poison layer is made of a non-catalytic porous material.

* * * * *